US008221492B2

United States Patent
Case et al.

(10) Patent No.: US 8,221,492 B2
(45) Date of Patent: Jul. 17, 2012

(54) ARTIFICIAL VALVE PROSTHESIS WITH IMPROVED FLOW DYNAMICS

(75) Inventors: Brian C. Case, Lake Villa, IL (US); Michael L. Garrison, Indianapolis, IN (US); Andrew Hoffa, Bloomington, IN (US); Darin G. Schaeffer, Bloomington, IN (US); Jacob A. Flagle, New Palestine, IN (US)

(73) Assignee: Cook Medical Technologies, Bloomington, IN (US)

( * ) Notice: Subject to any disclaimer, the term of this patent is extended or adjusted under 35 U.S.C. 154(b) by 734 days.

(21) Appl. No.: 10/554,494

(22) PCT Filed: Apr. 21, 2004

(86) PCT No.: PCT/US2004/012430
§ 371 (c)(1),
(2), (4) Date: Mar. 13, 2007

(87) PCT Pub. No.: WO2004/096100
PCT Pub. Date: Nov. 11, 2004

(65) Prior Publication Data
US 2007/0260327 A1    Nov. 8, 2007

Related U.S. Application Data

(60) Provisional application No. 60/530,781, filed on Dec. 18, 2003, provisional application No. 60/465,141, filed on Apr. 24, 2003.

(51) Int. Cl.
*A61F 2/24* (2006.01)
(52) U.S. Cl. ..................................... 623/1.24
(58) Field of Classification Search .......... 623/1.24, 623/2.1, 2.12, 2.14–2.19, 23.68
See application file for complete search history.

(56) References Cited

U.S. PATENT DOCUMENTS 3,736,598 A    6/1973    Bellhouse et al.
(Continued)

FOREIGN PATENT DOCUMENTS

EP    0850607    7/1998
(Continued)

OTHER PUBLICATIONS

U.S. Appl. No. 10/828,716, Case et al., Artificial Valve Prosthesis with Improved Flow Dynamics, Filed Aug. 30, 2004; Notice of Allowance mailed Jul. 14, 2009.
(Continued)

*Primary Examiner* — Thomas J Sweet
*Assistant Examiner* — Megan Wolf
(74) *Attorney, Agent, or Firm* — Buchanan Nipper

(57) ABSTRACT

An expandable venous valve having a support structure that configured to enlarge the area adjacent to the valve structure such that the flow patterns of retrograde flow are modified in a way that facilitates the flushing of the pockets at the base of the valve area to prevent stagnation of bodily fluid, which in the venous system, can lead to thrombus formation. The enlarged pocket areas can be created by forming an artificial sinus adjacent the valve structure in an unsupported section of vessel wall between two support frame section or the support frame can comprise an expanded-diameter intermediate or proximal section that forms an artificial sinus adjacent the valve structure. In another group of embodiments, the attachment pathway between opposing leaflets and the support frame and/or vessel wall comprises a proximal portion that places the leaflets in extended contact with one another and a distal portion forms a large angle with respect to the adjacent walls such that a large pocket is created at the base of the leaflets. In one embodiment, the attachment pathway extends distally along a pair of substantially parallel longitudinal attachment struts to create an extended leaflet contact area, then angles circumferentially and distally from the former along distal attachment struts to define the bottom edge of the leaflets.

19 Claims, 9 Drawing Sheets

U.S. PATENT DOCUMENTS

| | | | |
|---|---|---|---|
| 4,297,749 A * | 11/1981 | Davis et al. | 623/2.19 |
| 4,441,216 A * | 4/1984 | Ionescu et al. | 623/2.19 |
| 5,139,515 A | 8/1992 | Robicsek | |
| 5,197,979 A | 3/1993 | Quintero et al. | |
| 5,344,426 A | 9/1994 | Lau et al. | |
| 5,358,518 A | 10/1994 | Camilli | |
| 5,397,355 A | 3/1995 | Marin et al. | |
| 5,411,552 A | 5/1995 | Andersen et al. | |
| 5,500,014 A | 3/1996 | Quijano et al. | |
| 5,545,215 A | 8/1996 | Duran | |
| 5,591,197 A | 1/1997 | Orth et al. | |
| 5,607,465 A | 3/1997 | Camilli | |
| 5,709,707 A | 1/1998 | Lock et al. | |
| 5,713,953 A | 2/1998 | Vallana et al. | |
| 5,733,325 A | 3/1998 | Robinson et al. | |
| 5,755,781 A | 5/1998 | Jayaraman | |
| 5,824,045 A | 10/1998 | Alt | |
| 5,836,964 A | 11/1998 | Richter et al. | |
| 5,840,081 A | 11/1998 | Andersen et al. | |
| 5,843,117 A | 12/1998 | Alt et al. | |
| 5,855,600 A | 1/1999 | Alt | |
| 5,855,601 A | 1/1999 | Bessler et al. | |
| 5,876,445 A | 3/1999 | Andersen et al. | |
| 5,879,382 A | 3/1999 | Boneau | |
| 5,907,893 A | 6/1999 | Zadno-Azizi et al. | |
| 5,957,949 A | 9/1999 | Leonhardt et al. | |
| 6,033,398 A | 3/2000 | Farley et al. | |
| 6,053,940 A | 4/2000 | Wijay | |
| 6,123,721 A | 9/2000 | Jang | |
| 6,129,755 A | 10/2000 | Mathis et al. | |
| 6,132,460 A | 10/2000 | Thompson | |
| 6,132,461 A | 10/2000 | Thompson | |
| 6,146,416 A | 11/2000 | Andersen et al. | |
| 6,159,237 A | 12/2000 | Alt et al. | |
| 6,190,406 B1 | 2/2001 | Duerig et al. | |
| 6,200,336 B1 | 3/2001 | Pavcnik et al. | |
| 6,235,053 B1 | 5/2001 | Jang | |
| 6,241,763 B1 | 6/2001 | Drasler et al. | |
| 6,280,467 B1 | 8/2001 | Leonhardt | |
| 6,283,990 B1 | 9/2001 | Kanesaka | |
| 6,287,334 B1 | 9/2001 | Moll et al. | |
| 6,312,459 B1 | 11/2001 | Huang et al. | |
| 6,312,465 B1 | 11/2001 | Griffin et al. | |
| 6,315,793 B1 | 11/2001 | Bokros et al. | |
| 6,325,819 B1 | 12/2001 | Pavcnik et al. | |
| 6,328,763 B1 | 12/2001 | Love et al. | |
| 6,338,740 B1 * | 1/2002 | Carpentier | 623/2.13 |
| 6,340,366 B2 | 1/2002 | Wijay | |
| 6,342,067 B1 | 1/2002 | Mathis et al. | |
| 6,342,070 B1 | 1/2002 | Nguyen-Thien-Nhon | |
| 6,348,065 B1 | 2/2002 | Brown et al. | |
| 6,352,554 B2 | 3/2002 | De Paulis | |
| 6,355,056 B1 | 3/2002 | Pinheiro | |
| 6,440,163 B1 | 8/2002 | Swanson et al. | |
| 6,458,153 B1 | 10/2002 | Bailey et al. | |
| 6,488,702 B1 | 12/2002 | Besselink | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,514,063 B2 | 2/2003 | Acciai et al. | |
| 6,558,415 B2 | 5/2003 | Thompson | |
| 6,572,650 B1 | 6/2003 | Abraham et al. | |
| 6,582,462 B1 | 6/2003 | Andersen et al. | |
| 6,598,307 B2 | 7/2003 | Love et al. | |
| 6,613,086 B1 | 9/2003 | Moe et al. | |
| 6,663,661 B2 | 12/2003 | Boneau | |
| 6,669,724 B2 | 12/2003 | Park et al. | |
| 6,676,698 B2 | 1/2004 | McGuckin, Jr. et al. | |
| 6,678,962 B1 | 1/2004 | Love et al. | |
| 6,730,117 B1 | 5/2004 | Tseng et al. | |
| 6,786,922 B2 | 9/2004 | Schaeffer | |
| 6,790,237 B2 | 9/2004 | Stinson | |
| 6,821,292 B2 | 11/2004 | Pazienza et al. | |
| 6,878,162 B2 | 4/2005 | Bales et al. | |
| 6,958,076 B2 | 10/2005 | Acosta et al. | |
| 6,962,603 B1 | 11/2005 | Brown et al. | |
| 6,974,474 B2 | 12/2005 | Pavcnik et al. | |
| 6,976,995 B2 | 12/2005 | Mathis et al. | |
| 7,018,403 B1 | 3/2006 | Pienknagura | |
| 7,018,404 B2 | 3/2006 | Holmberg et al. | |
| 7,018,406 B2 | 3/2006 | Seguin et al. | |
| 7,025,777 B2 | 4/2006 | Moore | |
| 7,025,780 B2 | 4/2006 | Gabbay | |
| 7,044,966 B2 | 5/2006 | Svanidze et al. | |
| 7,060,088 B1 | 6/2006 | Fischell et al. | |
| 7,101,396 B2 | 9/2006 | Artof et al. | |
| 7,118,600 B2 | 10/2006 | Dua et al. | |
| 7,125,418 B2 | 10/2006 | Duran et al. | |
| 7,128,756 B2 | 10/2006 | Lowe et al. | |
| 7,128,759 B2 | 10/2006 | Osborne et al. | |
| 7,147,661 B2 | 12/2006 | Chobotov et al. | |
| 7,153,324 B2 | 12/2006 | Case et al. | |
| 7,160,320 B2 | 1/2007 | Duran | |
| 7,195,641 B2 | 3/2007 | Palmaz et al. | |
| 7,338,520 B2 | 3/2008 | Bailey et al. | |
| 7,347,869 B2 | 3/2008 | Hojeibane et al. | |
| 7,351,256 B2 | 4/2008 | Hojeibane et al. | |
| 7,354,455 B2 | 4/2008 | Stinson | |
| 7,377,938 B2 | 5/2008 | Sarac et al. | |
| 7,381,219 B2 | 6/2008 | Salahieh et al. | |
| 7,445,631 B2 | 11/2008 | Salahieh et al. | |
| 7,452,371 B2 | 11/2008 | Pavcnik et al. | |
| 7,524,331 B2 | 4/2009 | Birdsall | |
| 7,544,207 B2 | 6/2009 | Osborne et al. | |
| 7,547,322 B2 | 6/2009 | Sarac et al. | |
| 7,625,399 B2 | 12/2009 | Case et al. | |
| 2001/0016770 A1 | 8/2001 | Allen et al. | |
| 2001/0018610 A1 | 8/2001 | Limon | |
| 2001/0020183 A1 | 9/2001 | Jang | |
| 2001/0039450 A1 | 11/2001 | Pavcnik et al. | |
| 2001/0049553 A1 | 12/2001 | De Paulis | |
| 2002/0010504 A1 | 1/2002 | Alt | |
| 2002/0099439 A1 | 7/2002 | Schwartz et al. | |
| 2002/0111339 A1 | 8/2002 | Klausener et al. | |
| 2002/0123790 A1 | 9/2002 | White et al. | |
| 2002/0129820 A1 | 9/2002 | Ryan et al. | |
| 2002/0177894 A1 | 11/2002 | Acosta et al. | |
| 2002/0193871 A1 | 12/2002 | Beyersdorf et al. | |
| 2003/0069646 A1 | 4/2003 | Stinson | |
| 2003/0093144 A1 | 5/2003 | Jang | |
| 2003/0109922 A1 * | 6/2003 | Peterson et al. | 623/2.17 |
| 2003/0114919 A1 | 6/2003 | McQuiston et al. | |
| 2003/0139805 A1 | 7/2003 | Holmberg et al. | |
| 2003/0144670 A1 | 7/2003 | Pavcnik et al. | |
| 2003/0176914 A1 | 9/2003 | Rabkin et al. | |
| 2003/0187500 A1 | 10/2003 | Jansen et al. | |
| 2003/0208261 A1 | 11/2003 | Thorpe et al. | |
| 2003/0220683 A1 | 11/2003 | Minasian et al. | |
| 2003/0236568 A1 | 12/2003 | Hojeibane et al. | |
| 2004/0019374 A1 | 1/2004 | Hojeibane et al. | |
| 2004/0024444 A1 | 2/2004 | Moore | |
| 2004/0024447 A1 | 2/2004 | Haverich | |
| 2004/0044401 A1 | 3/2004 | Bales et al. | |
| 2004/0093061 A1 | 5/2004 | Acosta et al. | |
| 2004/0093070 A1 | 5/2004 | Hojeibane et al. | |
| 2004/0093073 A1 | 5/2004 | Lowe et al. | |
| 2004/0102834 A1 | 5/2004 | Nakano et al. | |
| 2004/0106985 A1 | 6/2004 | Jang | |
| 2004/0167619 A1 | 8/2004 | Case et al. | |
| 2004/0215333 A1 | 10/2004 | Duran et al. | |
| 2004/0225344 A1 | 11/2004 | Hoffa et al. | |
| 2004/0243218 A1 | 12/2004 | Schaeffer | |
| 2004/0254640 A1 | 12/2004 | Sutherland et al. | |
| 2004/0260389 A1 | 12/2004 | Case et al. | |
| 2005/0055079 A1 | 3/2005 | Duran | |
| 2005/0059923 A1 | 3/2005 | Gamboa | |
| 2005/0075713 A1 | 4/2005 | Biancucci et al. | |
| 2005/0096735 A1 | 5/2005 | Hojeibane et al. | |
| 2005/0216077 A1 | 9/2005 | Mathis et al. | |
| 2005/0222661 A1 | 10/2005 | Case et al. | |
| 2005/0228479 A1 | 10/2005 | Pavcnik et al. | |
| 2005/0234541 A1 | 10/2005 | Hunt et al. | |
| 2005/0234546 A1 | 10/2005 | Nugent et al. | |
| 2006/0015178 A1 | 1/2006 | Moaddeb et al. | |
| 2006/0074480 A1 | 4/2006 | Bales et al. | |
| 2006/0116572 A1 | 6/2006 | Case | |
| 2006/0136045 A1 | 6/2006 | Flagle et al. | |

| | | | |
|---|---|---|---|
| 2006/0178729 A1 | 8/2006 | Thielen et al. | |
| 2006/0178730 A1 | 8/2006 | Hill et al. | |
| 2006/0195004 A1 | 8/2006 | Jarvik | |
| 2006/0241744 A1 | 10/2006 | Beith | |
| 2006/0271159 A1 | 11/2006 | Gregorich et al. | |
| 2006/0276882 A1 | 12/2006 | Case et al. | |
| 2006/0287717 A1 | 12/2006 | Rowe et al. | |
| 2007/0260327 A1 | 11/2007 | Case et al. | |
| 2008/0082166 A1 | 4/2008 | Styrc et al. | |
| 2008/0249619 A1 | 10/2008 | Stacchino et al. | |
| 2009/0082858 A1 | 3/2009 | Nugent et al. | |
| 2009/0088836 A1 | 4/2009 | Bishop et al. | |
| 2009/0099653 A1 | 4/2009 | Suri et al. | |
| 2009/0240320 A1 | 9/2009 | Tuval et al. | |
| 2009/0248132 A1 | 10/2009 | Bloom et al. | |
| 2009/0270965 A1 | 10/2009 | Sinha et al. | |

FOREIGN PATENT DOCUMENTS

| | | | |
|---|---|---|---|
| EP | 0850607 A | | 7/1998 |
| WO | WO8302225 | | 7/1983 |
| WO | 0154625 | | 8/2001 |
| WO | WO 0154625 A | | 8/2001 |
| WO | 03030776 | | 4/2003 |
| WO | WO 03030776 A | | 4/2003 |

OTHER PUBLICATIONS

European Search Report and Search Opinion, issued by the European Patent Office, Nov. 9, 2009 for Application No. 09170581.4-2320.

Office Action Summary for U.S. Appl. No. 10/828,716, Issued by the USPTO, Dec. 31, 2008, pp. 1-8.

Office Action Summary for U.S. Appl. No. 12/614,878, Issued by the USPTO, Apr. 12, 2010, pp. 1-17.

Office Action Summary for U.S. Appl. No. 12/605,585, Issued by the USPTO, Apr. 14, 2010, pp. 1-21.

Office Action Summary for U.S. Appl. No. 11/586,285, Issued by the USPTO, Jul. 16, 2009, pp. 1-9.

* cited by examiner

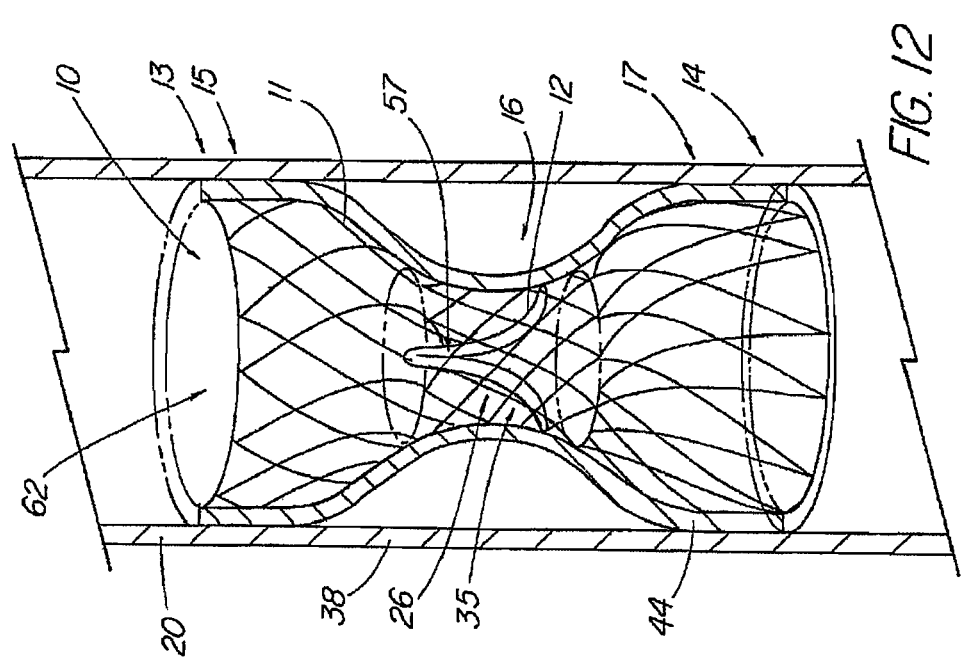
FIG. 12
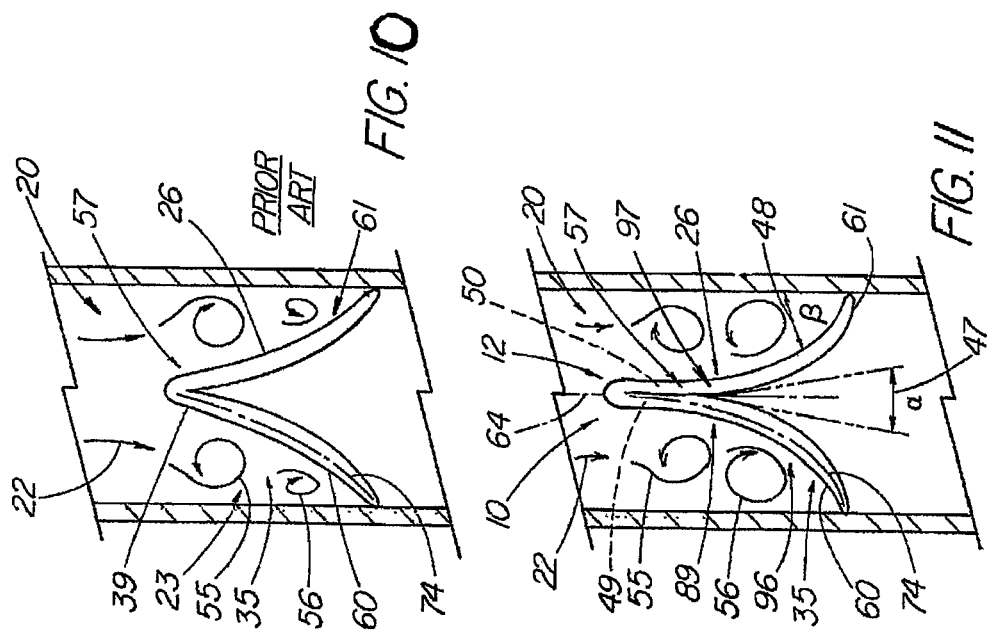
FIG. 10 PRIOR ART
FIG. 11

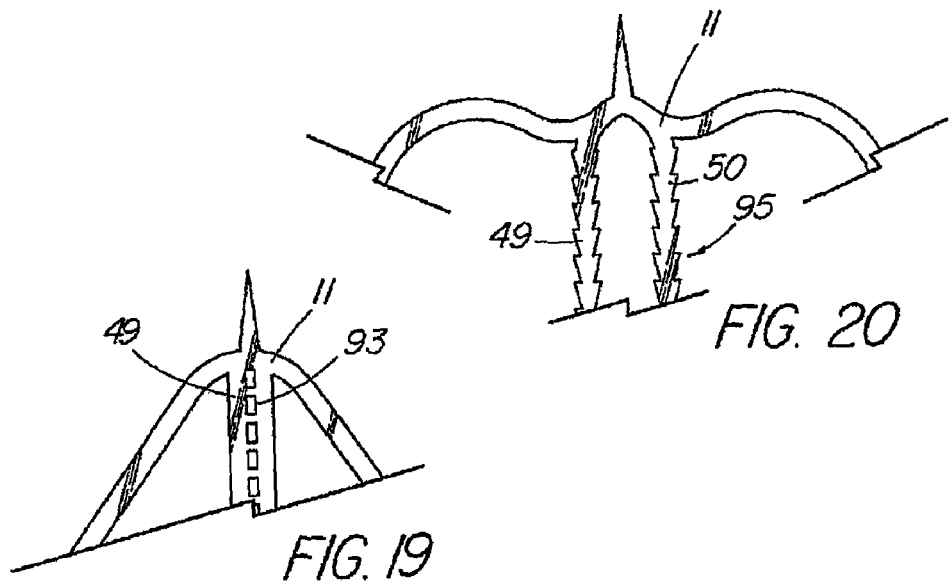
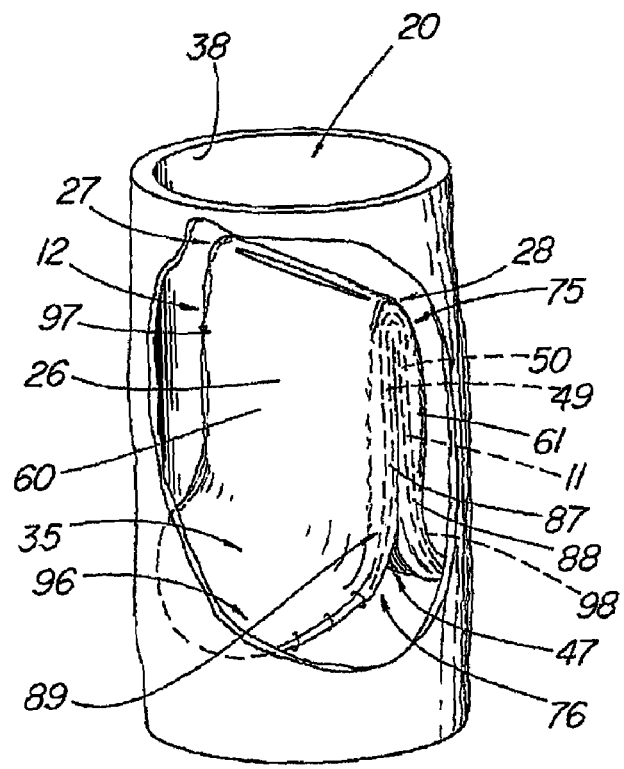

ARTIFICIAL VALVE PROSTHESIS WITH IMPROVED FLOW DYNAMICS

TECHNICAL FIELD

This invention relates to medical devices, more particularly to intravascular valve prostheses and the like.

BACKGROUND OF THE INVENTION

The venous system includes a series of valves that function to assist the flow of blood returning to the heart. These natural valves are particularly important in the lower extremities to prevent blood from pooling in the lower legs and feet during situations, such as standing or sitting, when the weight of the column of blood in the vein can act to prevent positive blood flow toward the heart. This condition, commonly known as 'chronic venous insufficiency', is primarily found in individuals in which gradual dilation of the veins, thrombotic events, or other conditions prevent the leaflets of the native valves from closing properly. This leads to significant leakage of retrograde flow such that the valve is considered 'incompetent'. Chronic venous insufficiency is a potentially serious condition in which the symptoms can progress from painful edema and unsightly spider or varicose veins to skin ulcerations. Elevation of the feet and compression stocking can relieve symptoms, but do not treat the underlying disease. Untreated, the disease can impact the ability of individuals to perform in the workplace or maintain their normal lifestyle.

To treat venous valve insufficiency, a number of surgical procedures have been employed to improve or replace the native valve, including placement of artificial valve prosthesis. These efforts have met with limited success and have not been widely adopted as a method of treating chronic venous insufficiency. More recently, the search has been to find a suitable self-expanding or radially-expandable artificial valve that can be placed using minimally invasive techniques rather than requiring open surgery and its obvious disadvantages. Thus far, use of prosthetic venous valves has remained experimental only.

While attempts have been made to mimic the function of the natural valve, there is no expandable valve for venous transcatheter placement that includes a combination of the native structural features that individually or collectively, may prove highly advantageous or critical for a successful valve. One common problem evident from early experiences with prosthetic valves is the formation of thrombus around the base of the leaflets, probably due at least in part to blood pooling in that region. In a natural valve, the leaflets are typically located within a sinus or enlargement in the vein. There is some evidence that the pockets formed between the leaflets and the walls of the sinus create vortices of flowing blood that help flush the pocket and prevent blood from stagnating and causing thrombosis around the valve leaflets, which can interfere with the function of the valve. It is thought that the stagnating blood prevents oxygen from reaching the endothelium covering the valve cusps, leading to hypoxia of the tissues which may explain increased thrombus formation typical in that location. Expandable-frame valve prostheses typically are of a generally cylindrical in shape and lack an artificial sinus or pocket space that is sufficient for simulating these natural blood flow patterns. What is needed is an intravenously placed artificial valve that is configured to create more effective flow patterns around the valve structure to circulate the blood or bodily fluids and reduce the likelihood of stagnation and the potential clinical problems that may result.

SUMMARY OF THE INVENTION

The foregoing problems are solved and a technical advance is achieved in an illustrative valve prosthesis, such as an artificial venous valve, having a valve structure and a self-expanding or otherwise expandable support structure that upon deployment within the vein, helps create an artificial sinus or larger pocket in the vessel surrounding the valve structure of sufficient size and shape to stimulate flow patterns or vortices which facilitate clearing of the blood or other bodily fluid that would otherwise pool therein. The structural adaptations result in more turbulent flow, increased velocity of flow, larger and/or more numerous vortices, other factors, or a combination of the above that prevent stagnant, hypoxic areas from occurring around the valve structure. Furthermore, the modified flow may also contribute to helping close the leaflets to form a seal and prevent leakage of fluid back through the valve. The artificial sinus or enlarged pockets simulate the function of the natural sinus that exists at the site of most natural valves in the deep veins of the lower legs and which may explain why the problem of thrombus forming around the valve structure has been observed to be a common problem in prosthetic venous valve designs lacking such a sinus area.

In one aspect of the invention, the collapsible support structure of the valve prosthesis is expandable to a particular diameter upon deployment, with the valve prosthesis being configured such that the prosthesis includes an intermediate, substantially 'open' section such that the artificial sinus is created by a portion of the duct or vessel that is substantially unsupported by the support structure. The unsupported portion of the vessel can advantageously assume a diameter that is larger than the deployment diameter of the vessel-anchoring or 'closed' sections or portions of the collapsible support structure, thereby creating an artificial sinus as blood (or bodily fluid) exerts pressure on the unsupported portion of the vessel wall. In one exemplary embodiment, the expandable support structure comprises a first, proximal portion and a second, distal portion that are interconnected by one or more thin members or struts, such that the largely unsupported region between the first and second (proximal and distal) sections of the support structure forms an artificial sinus (proximal being defined herein as have the same positional orientation as the orifice or opening of the valve structure, which is typically toward the heart in a venous valve). The valve structure is attached about the support structure such that it is largely situated within the unsupported region forming the artificial sinus. For example, the valve structure (defined herein as one or more cooperating leaflets, tubular members, or any flexible structure adapted to seal a passageway in response to changing fluid pressure differentials thereacross) may be attached to the interconnecting members, which can comprise oppositely placed struts having attachment points, (e.g., suture or any suitable structure or method) to facilitate attachment of the valve material.

In another aspect of the invention, the expandable support structure of the valve prosthesis comprises a framework or anchoring portion having an intermediate region that includes an enlarged diameter configured to create an artificial sinus about the valve structure, which is attached inside the intermediate region. In one embodiment, the support structure is made of a superelastic material, such as nitinol, and the intermediate region comprises an expanded or bulging portion that is formed by heat setting the nitinol tubular frame around a mandril or other fixture of the desired configuration using a method well known in the medical arts. The intermediate portion expands to a diameter larger than the proximal and distal portions when the prosthesis is deployed from the delivery system, thereby producing larger pockets around the valve structure which create more effective flow patterns to reduce pooling. In another embodiment, the proximal, distal, and intermediate sections are separate, interconnected sections, such as zig-zag frame or other expandable or self-expanding support or anchoring frames. The intermediate section comprising the artificial sinus includes a first and a second radially expandable or self-expanding portions in which the adjoining ends of each are larger in diameter than the ends which adjoin the proximal and distal sections, respectively. The frustoconical shape of the respective intermediate sections can be accomplished by either forming the section into that shape (i.e., plastic deformation of a tubular prosthesis, heat setting nitinol, laser cutting a frustoconical section of tubing, etc.) or a constraining means, such as a suture or thin wire, can be used to manipulate the relative diameters by feeding the constraining means through the apices of the bend or apertures therein and applying the appropriate amount of tension to create the desired shape. Optionally, a tubular or band-like section can be positioned between opposing frustoconical sections to create a longer artificial sinus.

In yet another aspect of the invention, the proximal end of the collapsible support at which the valve structure is located is expanded (e.g. flared outward) such that the expanded end or a combination of the expanded end and adjacent area of the vein forms the artificial sinus.

In still yet another aspect of the invention, the proximal and distal sections are configured to include a substantially open area between them with the valve structure being attached to the distal section such that it is positioned just below the artificial sinus. Optionally, a sleeve of a biomaterial (e.g a bioremodelable material such as small intestinal submucosa (SIS) or another collagenous extracellular matrix) or fabric can be attached over the proximal and distal sections such that it forms a seal between the prosthesis and the vessel wall, including the artificial sinus.

In still yet another aspect of the present invention, the support structure of the prosthesis is configured such that the attachment pathway (defined herein as the interface between the lateral, outer edges of the leaflets and the struts and/or vessel walls to which they are attached to establish and define the shape and configuration of the plurality of leaflets comprising the valve structure as deployed) has a first, proximal portion in which the one or more longitudinal attachment struts extending from the proximal bends or commissures that carry and support the proximal outer edges of the leaflets (and span the orifice) have a strongly longitudinal orientation with respect to the longitudinal axis of the prosthesis and valve structure, and a distal portion of the attachment pathway that extends circumferentially (laterally) and distally from the longitudinal axis to form the bottom or distal edge of the outer leaflet edge or perimeter. When viewed from the side, the support frame and attached leaflet is configured such that the angle (angle α) formed between the opposing leaflets, as carried along the proximal attachment pathway, is substantially less than the angle (angle β) formed between distal attachment pathways and the vessel walls. This configuration results in leaflets having large coaptable area relative to the overall surface area, which improves sealing (including reducing the effects of retraction by the valve material) and allows for larger pockets surrounding the leaflets which, like the sinus, facilitate the creation of larger, stronger vortices of retrograde flow that help close the leaflets and clear away blood or fluid that could otherwise stagnate under conditions where the surrounding pockets are smaller in size. As used herein, the term 'retrograde flow' is defined as bodily fluid traveling in a distal direction (toward the feet), whether due to gravitational forces, redirection due to contact with the prosthesis or bodily lumen walls, or by some other means.

A first embodiment of this aspect of the invention includes a frame comprising a pair of longitudinal attachment struts originating from each commissure bend. The struts extend in generally longitudinal direction, diverging relatively or not at all toward the distal end of the prosthesis before more acutely diverging as they curve laterally and circumferentially away from the proximal strut portions such that the transition between the proximal and distal portions of attachment pathway comprises a bend having a radius that is distinctly smaller than that of the adjacent strut portions (the proximal portions being straight some embodiments). The distal attachment pathways converge to define the bottom outer edge of each leaflet. In a second embodiment of this aspect of the invention, the support frame of the prosthesis includes a pair of substantially parallel longitudinal attachment struts to which the leaflets are attached to form the proximal portion of the attachment pathway, and distal attachment struts extending circumferentially and laterally outward from the substantially parallel struts to form the distal portion of the attachment pathway. The support frame carrying the valve structure may be advantageously comprised of radial sections (e.g., quadrants in a bicuspid valve) that are of an identical pattern but with alternating orientation such as to provide for radial stability and better expandability characteristics. The radial section not carrying the leaflet proximal outer edges serves as lateral support structure for adding longitudinal stability and help protecting the leaflets from adhering to the vessel walls. The parallel struts provide for advantageous bending and torsional characteristics such that the frame has utility as a stent. In an alternate embodiment of the support structure, the lateral outer edges of the opposing leaflets can be attached to single longitudinal attachment strut having a pair of distal struts extending laterally outward and circumferentially to carry the bottom half of the leaflet and define the overall shape thereof. The strut may be thicker than adjacent struts and include aperture therealong for facilitating attachment of the valve structure.

In still yet another aspect of the present invention, the proximal section of the valve is wider in diameter at its proximal end, which anchors the prosthesis in the vessel, and narrower at the interface between the proximal and intermediate sections. This, in combination with a leaflet structure that maximizes pocket size, results in retrograde flow being subject to a Venturi effect which increases flow and the strength of the vortices to close the valve and clear the pockets of potentially stagnating fluids.

The configuration of the basic units of the support structure and valve structure is not particularly critical for an understanding of the invention. Numerous examples are well known in the prior art and may be found in the disclosure of Applicant's provisional application Ser. No. 60/403,783 entitled, 'Implantable Vascular Device,' filed Aug. 15, 2002 which is expressly incorporated by reference herein.

BRIEF DESCRIPTION OF THE DRAWING

Embodiments of the present invention will now be described by way of example with reference to the accompanying drawings, in which:

FIGS. 10-11 depict side views comparing the flow patterns in a standard valve leaflet configuration with those of the embodiment of FIG. 9; and FIG. 12 depicts an embodiment of the present invention having a combination of a narrowed intermediate section and the valve structure configuration of FIG. 9.

FIGS. 19-20 depict plan views of adaptations in the support structure for affixing the valve structure thereto; and FIG. 21 depicts a partially sectioned perspective view of an embodiment in which the support structure does not co-extend along the entirety of the leaflet outer edges.

DETAILED DESCRIPTION

Figure 2:
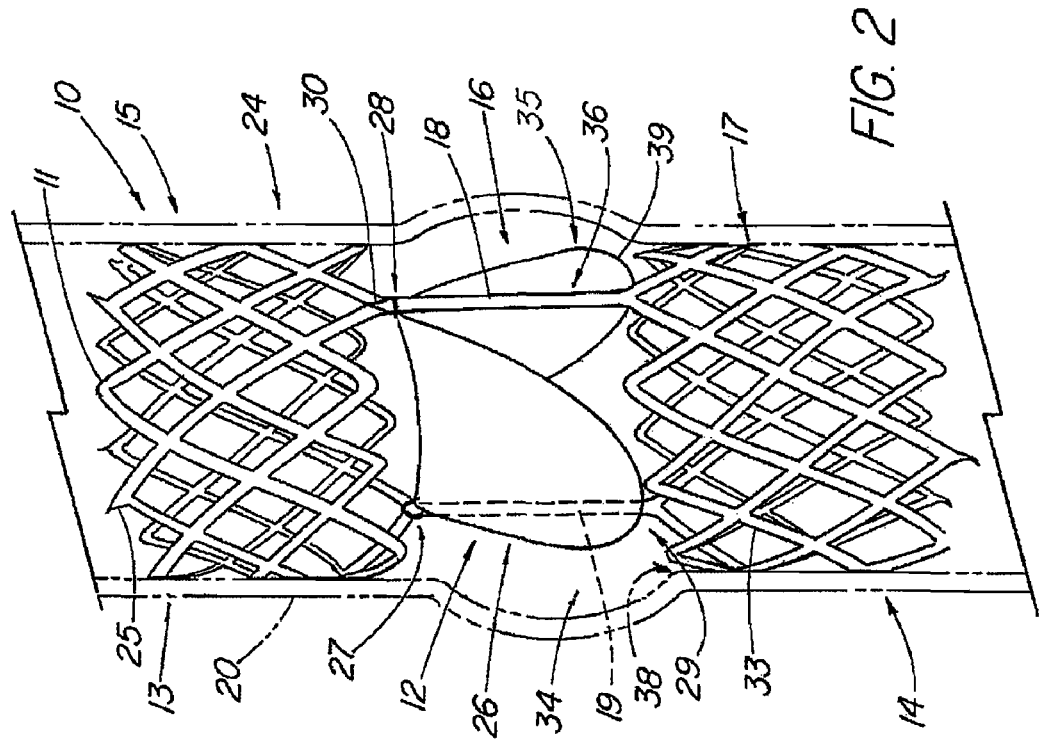
FIG. 2 depicts a schematic view of an illustrative embodiment of the present invention in which the prosthesis includes interconnecting proximal and distal sections defining an intermediate, substantially open section for creating an artificial sinus in the vessel.

The present invention, selected examples of which are illustrated in FIGS. 2-9, 11-20, comprises a collapsible, self expanding or otherwise expandable artificial valve prosthesis 10 that is deployed within a bodily passageway 20, such as a vessel or duct, of a patient typically delivered and implanted using well-known transcatheter techniques for self-expanding prostheses, the valve prosthesis having a first or proximal end 13 and a second or distal end 14, with the normal, antegrade fluid flow typically traveling from the distal end to proximal end of the prosthesis, the latter being located closest to the heart in a venous valve when placed within the lower extremities of a patent. The valve prosthesis 10 comprises a support structure 11 and a valve structure 12, such as the illustrative valve structure, attached about the support structure and configured to selectively restrict fluid flowing therethrough by closing with changes in the fluid pressure differential, such as in the presence of retrograde flow. The present invention includes structural features that modify the flow dynamics within the prosthesis such that fluid collecting in pockets 35 near the base of the leaflets 26 is more likely to be flushed away or effectively mixed with fresher incoming bodily fluid on a continual basis.

It should be understood that the materials used to comprise the support structure 11 can be selected from a well-known list of suitable metals and polymeric materials appropriate for the particular application, depending on necessary characteristics that are required (self-expansion, high radial force, collapsibility, etc.). The materials used for the valve structure 12 can comprise a synthetic material or biologically-derived material appropriate for the clinical application; however, investigational studies have demonstrated that a bioremodelable material (such as an collagenous extracellular matrix (e.g., small intestinal submucosa), pericardial, or a growth factor-enhanced material may have superior anti-thrombogenic properties within the body as the native cells and tissue gradually replace the original leaflet material. The number of leaflets possible for embodiments of the present invention can be two, three, four, or any practical number, but bi-leaflet valves may prove advantageous in low-flow venous situation as compared to tri-leaflet embodiments, such the type used as heart valves which are subject to high-flow situations where thrombus formation is far less of a problem.

Figure 1:
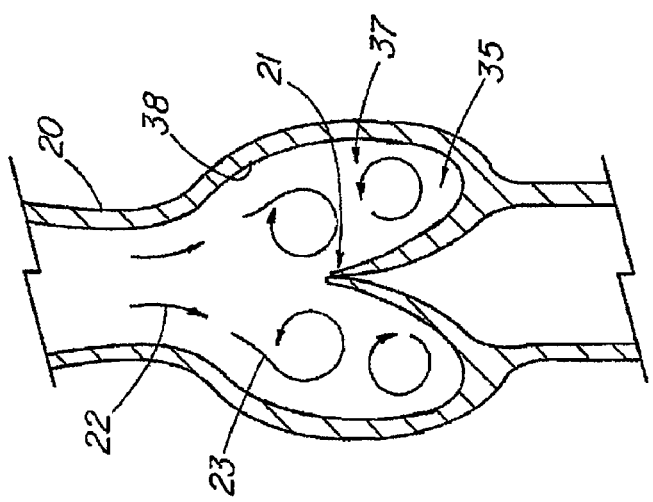
FIG. 1 depicts a cross-sectional view of a native venous valve and retrograde blood flow pattern.

In the embodiments of FIGS. 2-8, the support structure 11 is configured such that when the device is deployed within the bodily passage 20, such as a vein of the lower legs or feet, an artificial sinus 34 is formed adjacent to and surrounding the valve structure 12 such that the blood or other bodily fluids collecting within the pockets 35 formed around the bases of the valve leaflets 26 is more likely to be flushed out on a continual basis due to the advantageous geometry created by the artificial sinus 34. The principle is illustrated in the example of FIG. 1 which shows a natural venous valve 21 in which retrograde blood 22 flowing or falling back down and closing the valve is thought to create a series of vortices 23 as it contacts the leaflets. It is believed that the rounded shape of the enlarged natural sinus 37 surrounding the valve 21 facilitates creation of these vortices, thereby preventing blood from pooling or stagnating within the pockets 35 at the base of the valve 21, which may lead to thrombus formation or other problems. The present invention, by virtue of the configuration of the support structure 11, creates an artificial sinus 34 that attempts to reproduce the function served by the natural sinus 37 in the vein.

FIG. 2 depicts a side view of an illustrative embodiment of the present invention in which the prosthesis 10 includes a first or proximal section 15 and a second or distal section 17 that are spaced apart from one another, defining an intermediate, substantially open section 16 for creating the artificial sinus 34 in the vessel 20. The term 'substantially open' is used herein to define a largely unsupported portion of the bodily passage in which at least some minimal interconnecting structure (e.g., thin or flexible elements aligned with the leaflet commissures) is present that traverses the unsupported portion of the bodily passage, but it comprises very limited surface area and typically supplies minimal, if any, force against the walls of the passageway lateral to the valve structure 12. The proximal and distal sections 15,17, which preferably comprise a pair of radially expandable or self-expanding anchoring portions 24, are joined by an interconnecting means 36, such as the illustrative pair of connection struts 18,19 that allows the intermediate section 16 to be otherwise open and free of scaffolding so that the vein walls 38 along that section of the vessel 20 are able to expand due to pressure exerted by the blood flowing within the vein.

In the embodiments of the present invention, the anchoring portions 24 may function as stents to help the bodily passage remain patent, but their primary function is limited to engaging the bodily passage to anchor the prosthesis thereagainst. The support structure 11 and anchoring portions 24 also may be configured to be readily collapsible as with a normal vein. Since the diameters of the proximal and distal sections 15,17 generally assume a fixed diameter after deployment, the intermediate section, which is mostly unsupported or covered by structure, expands to form a bulging region of the vessel that functions as an artificial sinus 34. Although the interconnecting means 36 advantageously permit the proximal and distal sections 15,17 to be deployed together at a fixed distance from one another, it is within the scope of the invention to have the valve prosthesis 10 comprise separate unconnected sections that are deployed sequentially at an effective distance from one another to create an artificial sinus 34 therebetween. Additionally, the interconnecting means 36 can comprise suture, fabric, or some other non-rigid material to join the proximal and distal sections 15,17 and define the optimal length of the intermediate section 16, without interfering with the creation of the artificial sinus 34. To deploy a prosthesis 10 having a flexible interconnecting means 36, one of either the proximal or the distal sections 15,17 can be deployed first with the delivery system then being slowly withdrawn until the interconnecting means 36 becomes taut, whereby the opposite section is then deployed.

In the illustrative embodiment, the valve structure 12 comprises a pair of leaflets 26 that are situated in the intermediate section and attached to the proximal section 15 at two commissural points 27,28, each located at the proximal ends of the interconnecting struts 18,19, using an appropriate attachment means 30, such as suture, adhesive, fasteners, tissue welding using heat and/or pressure, etc. The leaflets 26 are attached about their distal ends 29 to the distal section 17 of the support structure 11 using the same or an other suitable attachment means 30. The valve structure 12 is configured so that it advantageously expands with the deployment of the proximal and distal sections 15,17 such that the outer edges 39 thereof contact the vessel wall sufficiently to at least substantially prevent leakage of bodily fluid around the valve structure 12. Optionally, the wall-engaging outer edges of the leaflets 26 can be reinforced with a separate frame 32 that is attached to or incorporated into the outer edges 37 to improve sealing with the vessel wall 38. An example of such a frame 32 is depicted in embodiment shown in FIG. 3 in which the frame 32 also serves as the interconnecting means 36 between the proximal and distal section 15,17 of the support structure 11, with the struts 18,19 being laser cut from the same tube used to form the remainder of the support structure 11. The valve frame 32 (that portion of the support structure 11 that reinforces the valve structure 12) can either be configured to exert relatively little radial force beyond what might be required to ensure adequate contact with the vessel wall 38, or it may be configured such that the frame 32 exerts sufficient radial force such that it assists in creating an artificial sinus 34 in the portion of the vein along the intermediate section 16 of the valve prosthesis 10.

Figure 4:
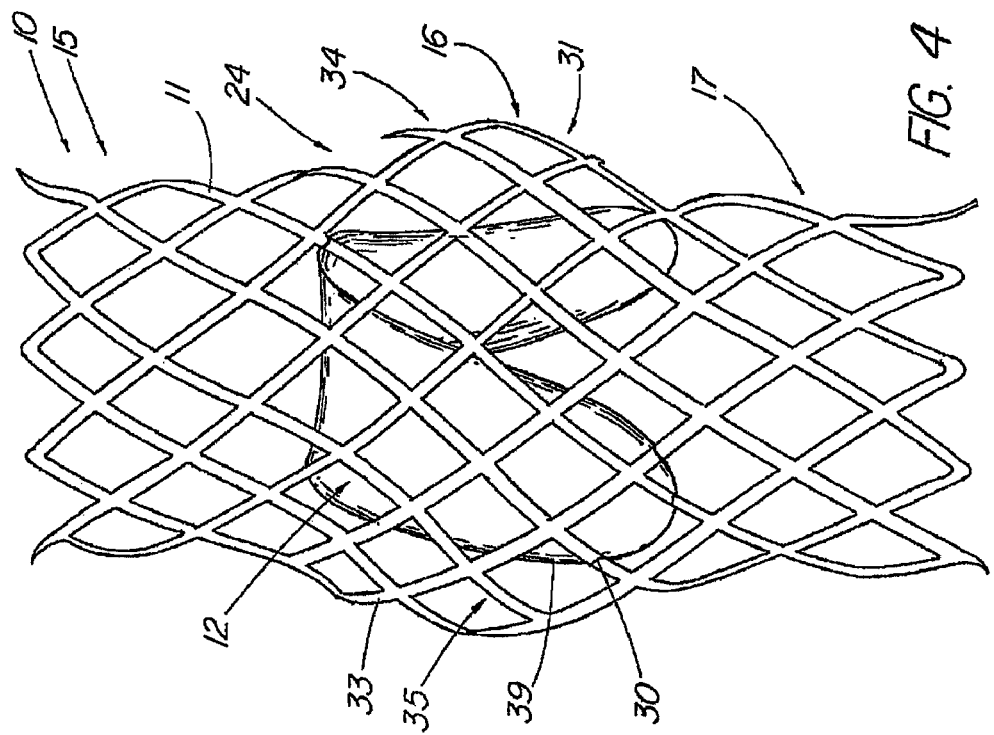
FIG. 4 depicts a schematic view of an illustrative embodiment of the present invention in which the intermediate section of the prosthesis comprises an expanded portion of the support structure.
Figure 3:
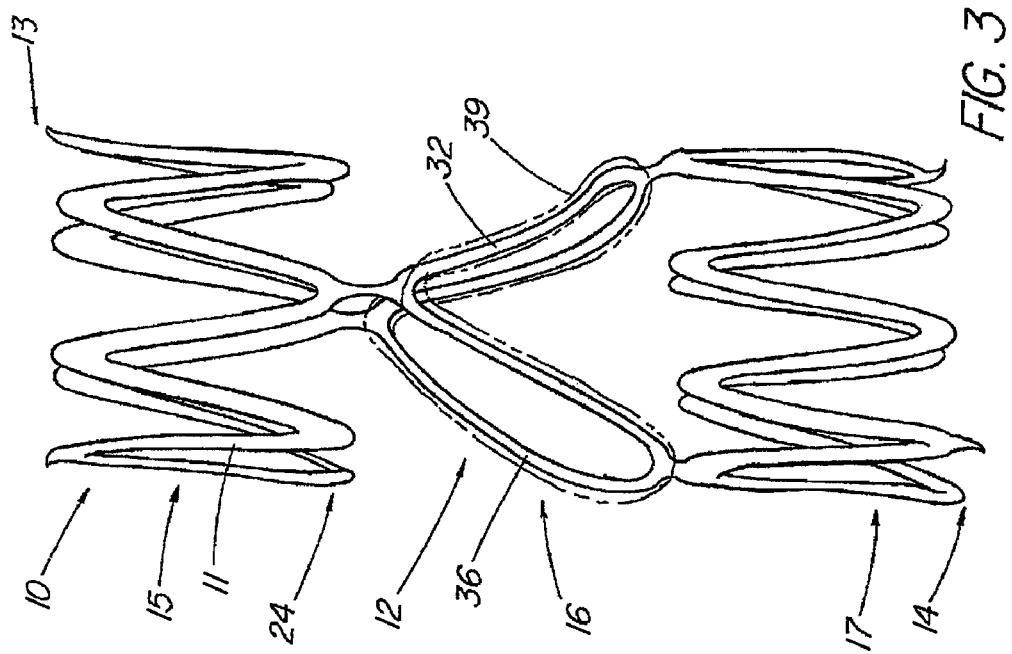
FIG. 3 depicts a schematic view of a second illustrative embodiment of the present invention in which the proximal and distal sections are interconnected by a frame that is incorporated into the valve structure of the prosthesis.
Figure 5:
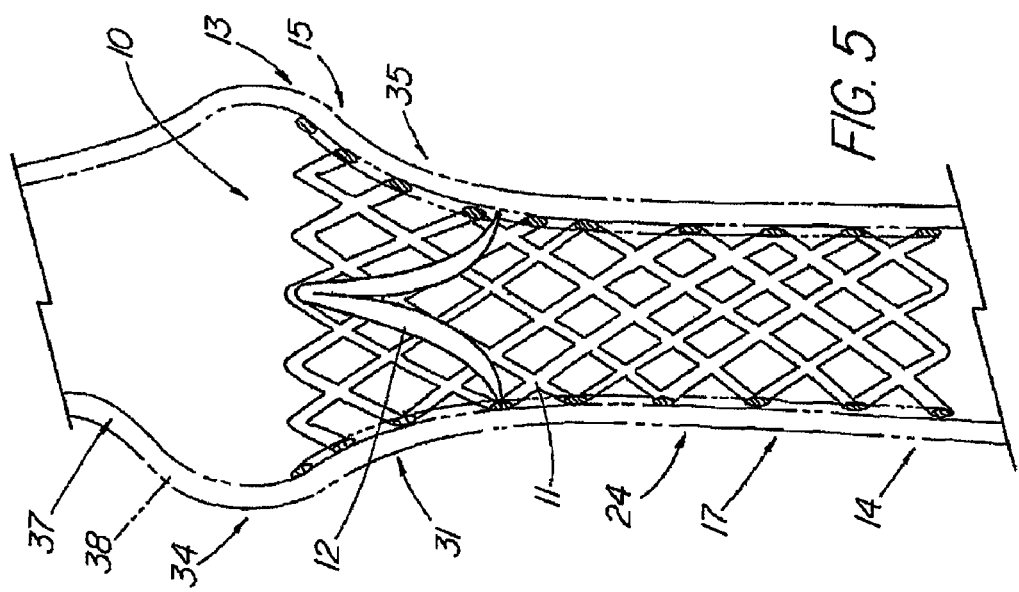
FIG. 5 depicts a schematic view of an illustrative embodiment of the present invention in which the proximal end is expanded to create an artificial sinus about the valve structure.

Another method of creating the artificial sinus 34 is depicted in FIGS. 4-5, whereby the support structure 11 includes an expanded portion 31, larger in diameter than the remainder of the support structure 11, that upon deployment, creates an artificial sinus 34 surrounding the valve structure 12. The diameter of the artificial sinus 34 caused extending the vessel wall 38 is, at its widest point, preferably about 10-120% larger than the diameters of the proximal and distal sections 15,17 when fully deployed (unrestrained from within the delivery sheath), with a more preferred differential of about 30-80% and a most preferred difference of 50-70% larger, depending on the diameter of the vein, the valve structure geometry, fluid column pressures at that location, and other factors. In the illustrative embodiments, the transition between the proximal and distal section 15,17 and the expanded intermediate section 16 is curvilinear, creating a bulge-like or flared configuration (FIGS. 4 and 5, respectively). In the examples depicted, the support structure comprises a single tubular anchoring portion 24 that is plastically, resiliently, or otherwise deformed into a second configuration that includes the expanded portion 31. For example, the anchoring portion 24 can be laser cut from a tube of nitinol, placed around a mandril having the desired shape, and heat set to produce the final desired shape. In the embodiment of FIG. 4, the expanded portion 31 comprises the intermediate section 16 of the prosthesis 10, such that the artificial sinus 34 is created between the proximal and distal sections 15,17 and the valve structure 12 is located therein. In FIG. 5, the expanded portion 31, which comprises the proximal section 15 of the support structure 11, includes a flared configuration that extends outward from the distal section 17 (no separately functional intermediate section 16 is present). The valve structure 12 is attached about the proximal end 13, while the flared, expanded portion 31 thereabout causes the vessel 20 to bulge outward, thus creating an artificial sinus 34 about the proximal end of the prosthesis 10. The artificial sinus 34 comprises a combination of a supported and an unsupported portion in the embodiment of FIG. 5. In both illustrative embodiments the valve structure 12 is sewn to the struts 33 of the support structure within the passageway of the anchoring portion 24. Other alternative methods of attachment include adhesives, staples or other fasteners, wire, engagement barbs on the frame, tissue welding, etc.

Figure 7:
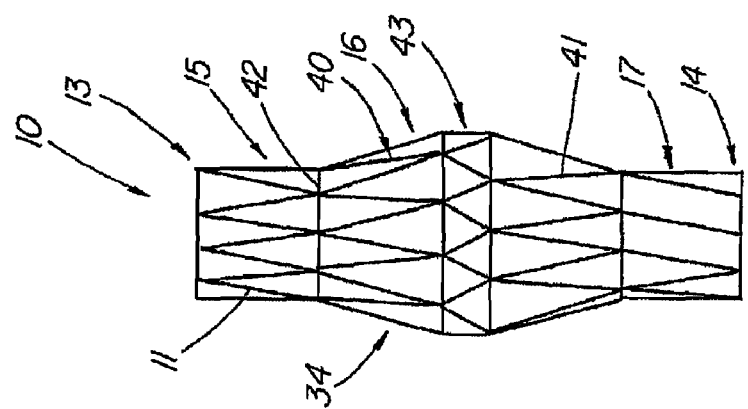
FIGS. 6-7 depict side views of embodiments of the present invention in which artificial sinus comprises a plurality of separate support sections.
Figure 6:
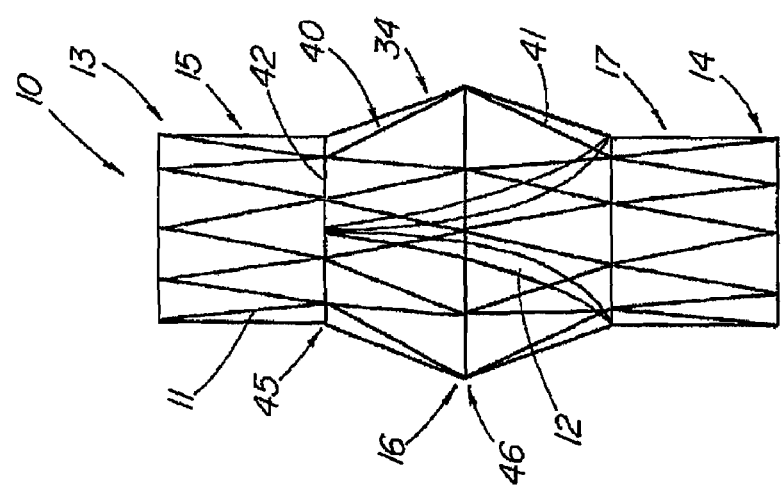

FIGS. 6-7 depict embodiments similar to that of FIG. 5, except that the proximal, intermediate, and distal sections 15,16,17 comprise separate anchoring portions 24 (having a serpentine or 'zig-zag' configuration in the illustrative embodiment) that are attached to one another in well-known manner, such as by feeding the illustrative thread material 42 or suture through the apices 45 of adjoining bends and securing it therearound. In the embodiment of FIG. 6, the intermediate section 16 comprises a first and a second intermediate subsection 40,41 of opposing frustoconical-shaped anchoring portion 24 that are coupled to form the artificial sinus 34. The first and second subsections 40,41 can be manipulated into a frustoconical shape by plastically deforming the anchoring portion 24 into that shape, or by increasing constraint of the frame about the distal end of a cylindrical-shaped proximal portion 15 and the proximal end of a cylindrical-shaped distal portion 17 with a constraining means 42, such as thread, suture, wire, band, covering, etc., so that the respective sections 15,17 assume a frustoconical shape. Additional constraining means 42 may be included at the first and second ends 13,14, as depicted, to maintain the cylindrical shape of the proximal and distal 15,17 sections. The thread or suture 30 (constraining means) at the interface 46 interconnecting the first and second intermediate subsections 40,41 may or may not function to tension the apices 45 of those respective subsections. The illustrative embodiment of FIG. 7 is similar to that of FIG. 6 except that the intermediate section 16 also comprises a third intermediate subsection 43, located between intermediate subsection 40 and 41, that extends the length of the artificial sinus. The illustrative third intermediate section 43 comprises a short cylindrical or band-shaped portion whose width can be adjusted to create the desired geometry of the artificial sinus 34. Additional subsections can be added as well, if so desired.

Figure 8:
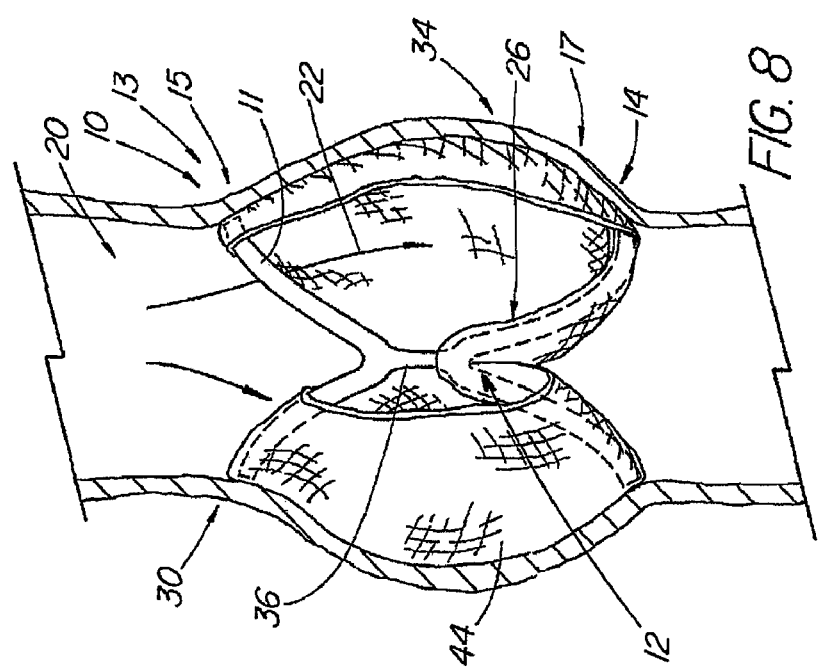
FIG. 8 depicts a partially sectioned side view of an embodiment of the present invention that includes an external sleeve of material.

FIG. 8 depicts an embodiment in which the support structure 11 comprises a proximal portion 15 joined to a distal portion 17 by a interconnecting strut 36, the entire support structure being cut from a single piece of cannula, such as stainless steel or nitinol. The valve structure 12, comprising a plurality of leaflets 26, is attached to the distal portion 17 such that the artificial sinus 34 is formed in the largely open, unsupported region between the proximal and distal sections 15,17 by virtue of the vessel 20 bulging outward, as in the embodiment of FIG. 2. The valve prosthesis 10 further includes an optional covering 44, such as an outer sleeve of SIS (or other suitable biological or synthetic material), that is attached to both the proximal and distal sections 15,17 of the support structure 11, which helps seal the prosthesis to prevent leakage of retrograde fluid therearound. The covering 44 is preferably of a constitution and configuration such that it does not interfere with the creation of the artificial sinus 34.

FIGS. 9,11, and 13-20 comprise embodiments of an artificial valve prosthesis 10 in which support structure 11 carrying the leaflets 26 is configured to increase the leaflet contact (coaptable) area 57 about the proximal portion of the valve structure 12 without relying on built-in slack within the material to bring the leaflets in closer proximity and provide for a extensive sealing area, longitudinally. As defined in this application, the leaflet contact area 57 comprises a longitudinal portion along the valve structure 12 in which the facing surfaces of opposing leaflets 26 (two or more) coapt or lie in close proximity to one other while in a dry or resting, neutral state (i.e., the pressure differentials across the valve orifice are essentially equalized such that the leaflets are not being forced together or apart due to external forces, such as fluid flow), when the prosthesis is an expanded or deployed configuration. The support frame 11 may be configured for maximizing the extent of the leaflet contact area 57 by including one or more longitudinal attachment struts 49,50 that define at least the proximal portion 75 of the attachment pathway 74 of each leaflet lateral outer edge 87,88 (the terms outer edge 39 and lateral outer edges 87,88 being defined herein as the area or zone along the leaflet that comprises the sealing interface). The longitudinal attachment struts 49,50/proximal attachment pathways 75 have a substantially longitudinal orientation (e.g., substantially parallel) with respect to the longitudinal axis 64 of the prosthesis (and valve structure 12). At a point generally proximate the distal end 89 of the leaflet contact area 57 (the proximal portion 96 of the leaflet), the distal portions 76 of the adjacent attachment pathways 74 (which are joined proximally about a commissural point) diverge from one another (forming a generally Y-shaped pathway configuration) and assume a much more circumferential orientation than that of the proximal portion 75 of the pathway such that the outer leaflet lateral edges 87,88 of each leaflet converge at a point lateral to the free inner edge 84 thereof to seal the passageway and form the distal portion 96 of the leaflet that defines the bottom 96 or 'floor' of the pocket 55 or intravascular space adjacent the outer surfaces of each of the leaflets, which generally assumes a strongly cupped or curved shape such that the leaflet assumes a generally 'folded' appearance due to the acutely angled attachment pathway 74 with the proximal portion of the leaflet having a strong longitudinal orientation with respect to the prosthesis and vessel and the bottom portion 96 having a strongly perpendicular orientation relative to the longitudinal axis of the vessel and prosthesis. It should be noted that the commissures 27,28, while located about the proximal end 13 of the illustrative prosthesis 10, may be located proximal thereto such that additional support structure 10 extends proximally, such as in the embodiments of FIGS. 2-8,12.

By extending or maximizing the leaflet contact area and decreasing the radius of the curvature of the leaflet (increasing curvature) about the distal portion thereof, the basal or distal portion of the pocket 35 adjacent each leaflet is enlarged to facilitate and maximize the size and/or velocity of the flow vortices 55,56 formed therein during retrograde flow. During pre-clinical investigations, these broader pockets have been shown to be especially advantageous in bi-leaflet artificial valve designs implanted in the venous system, these valves exhibiting a marked reduction in thrombus formation as compared to earlier designs. The improvement in flow dynamics for the purpose of clearing the pocket 35 of stagnant blood that can thrombose and compromise valve function or lead to other complications is depicted in a comparison of FIGS. 10 and 11. Laboratory analysis of the patterns of retrograde flow within a valve has shown that multiple vortices are typically created. In the embodiment of FIG. 10, which has a generally (inverted) V-shaped attachment pathway 74, a first vortex 55 is created below which a second, smaller vortex 56 is usually present, usually having opposite flow, which may be at least partially inadequate for clearing away blood pooling about the base of the leaflets 60,61 in a venous valve. In the embodiment of the present invention depicted in FIG. 11, which has a generally (inverted) Y-shaped attachment pathway 74, the larger pocket (at least at the basal portion) allows for a larger and stronger second vortex 56 of fluid created by retrograde flow that is more optimal for clearing away any pooling blood that would otherwise collect there and potentially provide for greater downforce on the leaflets 60,61 to improve closure of the valve.

Figure 9:
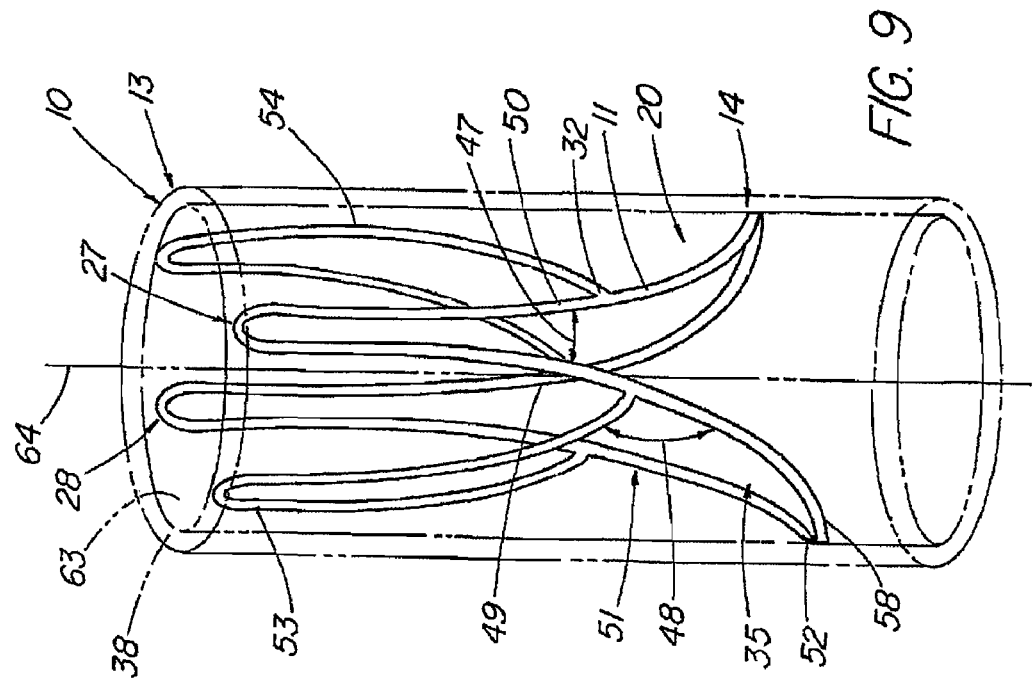
FIG. 9 depicts a perspective view of a support structure of the present invention adapted to increase coaptation of leaflets and pocket size within the vessel.

FIGS. 9 and 11 depict an artificial venous valve prosthesis 10 in which the frame 32 of the support structure 11 is configured such that the pair of longitudinal attachment struts 49,50 extending from each of the commissures 27,28 that represent the proximal attachment points for the valve structure (not shown) form a first angle 47 ($\alpha$) with respect to one another that is less than the second angle 48 ($\beta$) that is formed between the distal attachment struts 51,52, which comprise continuations of the longitudinal attachment struts 49,50 (together comprising the legs 58 of the frame 32), and the inside 63 of the vessel wall 38. The first angle 47 is preferably between −10 and 30° (a negative angle being possible with a sufficiently large-radius bend about the commissure) with a more preferred angle being 0-25° and a most preferred angle of 0-10°. The longitudinal attachment struts 49,50 may both diverge and converge at various points therealong (i.e., bow inward or outward), which in case, the first angle may be relevant for only the proximal portion 75 or is measurable between vectors representing the best straight line longitudinally traversing each strut 49,50. The illustrative embodiment also includes a pair of optional stabilizing arms 53,54 that extend laterally from the legs 58,59 to help center the prosthesis 10 within the vessel 20. Ideally, the angles depicted in the frame 32 configuration of FIG. 11 results in the opposing leaflets 60,61 being much more in alignment (e.g., parallel) with one another than in a prosthesis where the angles 47,48 are relatively the same, such as the prior art valve shown in FIG. 10, particularly over the proximal half of the leaflets 60,61. The result is the creation of a larger pocket around the base of the leaflets 60,61 that helps create larger and/or stronger vortices of retrograde blood flow. A second clinical benefit is that there is a larger area of coaptation between the leaflets 60,61, which helps provide a better seal against possible reflux through the valve orifice.

FIGS. 13-18 depict another group of embodiments configured for maximizing the coaptation distance or region between the leaflets in which the attachment pathway 74 comprises a proximal portion 75 that generally extends along one or more longitudinal attachment struts 49,50 that are generally aligned with the longitudinal axis 64 of the prosthesis and a distal portion 76 that is angled laterally from the longitudinal attachment struts and generally follows the distal attachment struts 51,52 which unlike the embodiment of FIG. 9, extend laterally outward from the longitudinal struts 49,50 as separate struts. As with the embodiment of FIG. 9, the distal attachment struts/portions converge at a point oppositely facing each leaflet 60,61 where they attach to the lateral support structure 53,54, which helps center the prosthesis in the vessel and protects the leaflets from adhering to the vessel wall. In the embodiments of FIGS. 13-17, the support frame 11 further includes proximal support arms 77,78 that attach to and extend from the longitudinal attachment struts 49,50 about the commissure points 27,28 and provide an interconnection with the lateral support structure 53,54 (also shown in FIG. 15).

Figure 13:
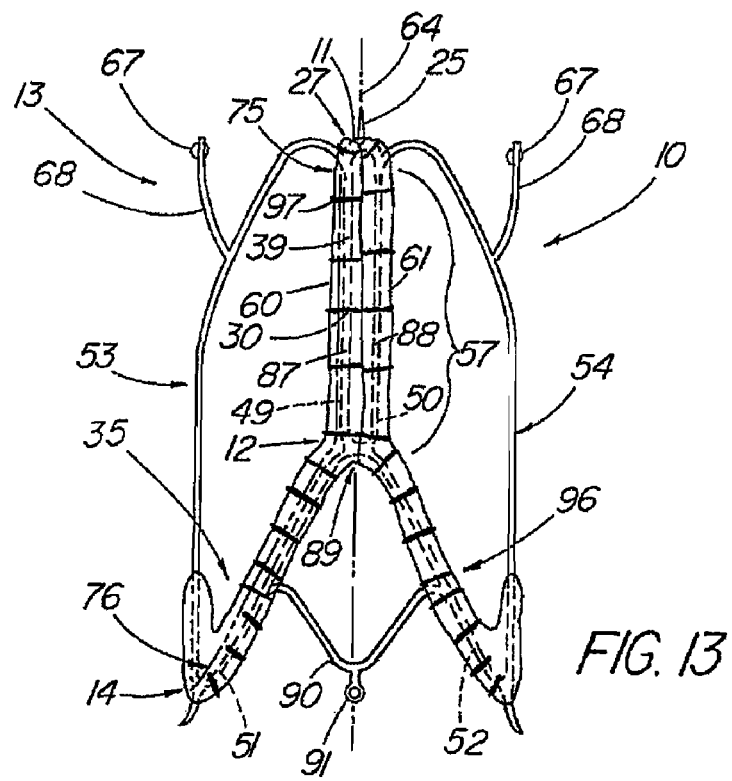
FIG. 13 depicts a side view of an embodiment of the present invention in which the leaflets are attached to the parallel struts to increase the area of coaptation.
Figure 14:
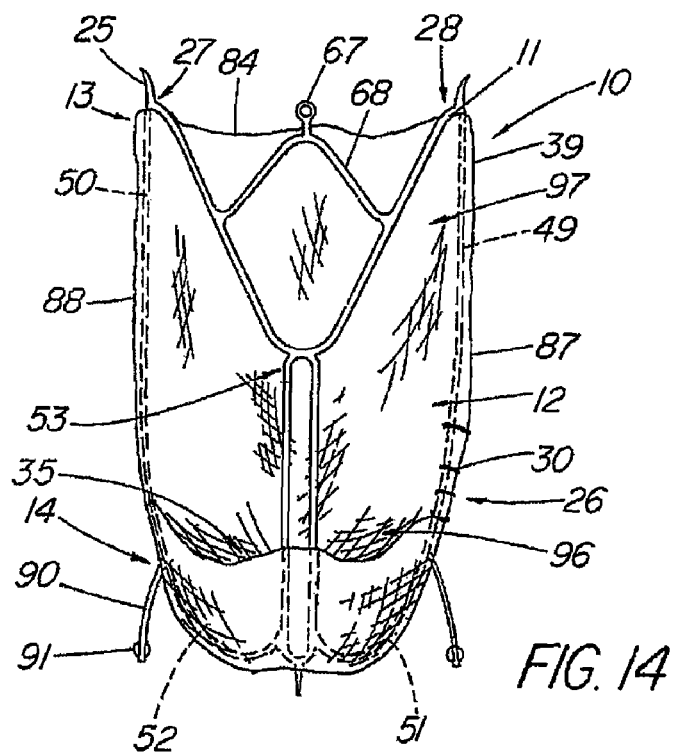
FIG. 14 depicts a side view of the embodiment of FIG. 13 that is rotated 90° therefrom.
Figure 15:
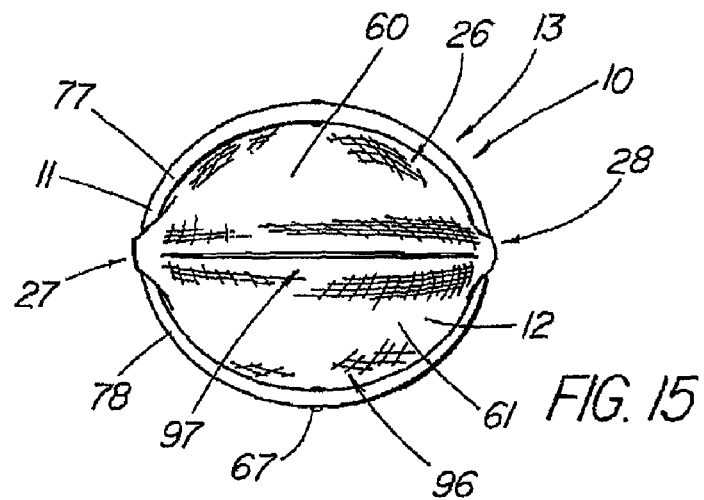
FIG. 15 depicts a top view of the embodiment of FIG. 13.
Figure 16:
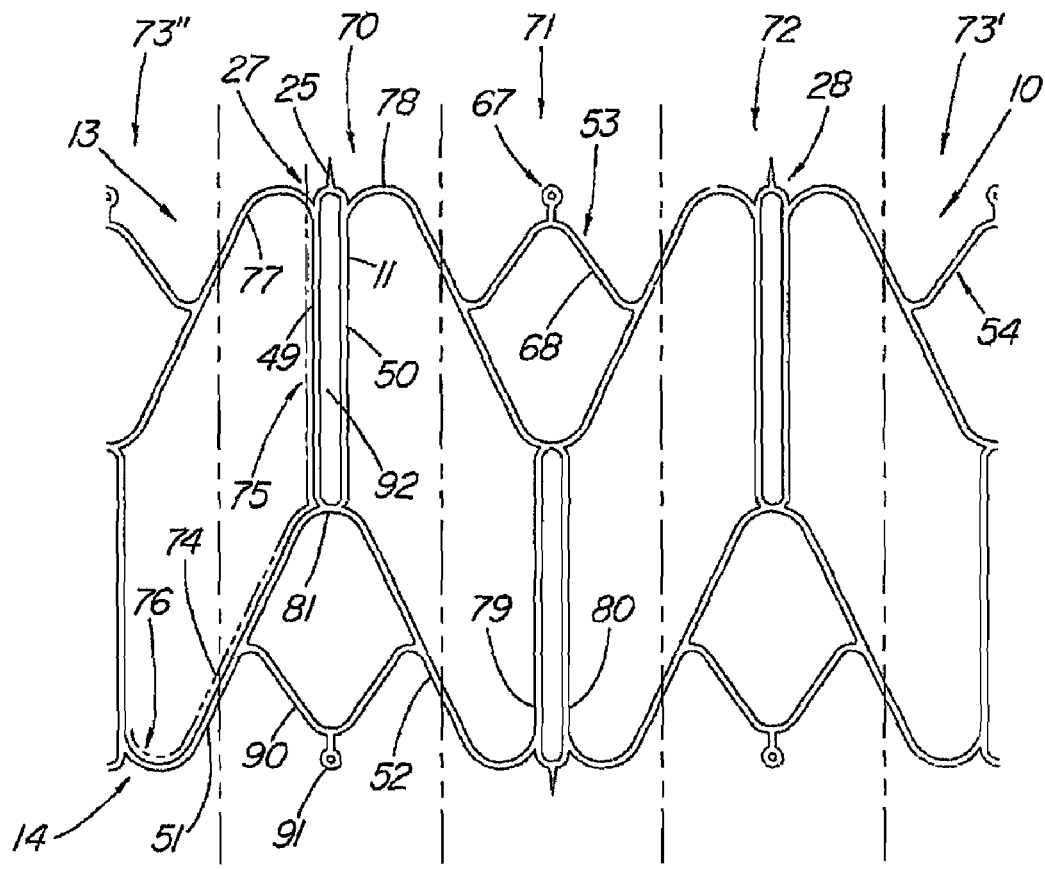
FIG. 16 depicts an unrolled view of the support frame of the embodiment FIG. 13.

The embodiment depicted in FIGS. 13-14 comprises a pair of longitudinal attachment struts 49,50, generally parallel to one another, which are adapted for attaching the respective leaflets 26 therealong, thus creating a large leaflet contact or coaptable area 57 that extends over half of the length of the prosthesis. As depicted in FIG. 16, The lateral support structure 53,54 shares or mirrors the configuration of the longitudinal attachment strut regions which they interconnect, except that they are located 90° therefrom and oriented oppositely thereto, such that the support structure 11 generally forms a serpentine configuration adapted to be readily collapsible and expandable. In the illustrative embodiment, the support structure 11 or frame can be divided into four sections or quadrants 70,71,72,73 that are identical except for their orientation, sections 70 and 72 being oriented with the commissures 27,28 and longitudinal attachment struts 49,50 carrying the valve structure 12 being oriented proximally toward the first end 13 of the prosthesis 10. The repeating, uniform design of the support structure 11 of the illustrative embodiment advantageously provides better structural stability, compressibility/expandability, and overall integrity than a support structure that does that comprise a non-uniform, non-repeating frame pattern.

The lateral arms 77,78 of the lateral support structure 53,54, that connect to the longitudinal attachment struts 49,50 each include a strut 68 that carries a proximal radiopaque marker 67 used to facilitate orientation of the device 10 and provide additional support. An identical distal strut 90 and an optional radiopaque marker 91 is located distal to the longitudinal attachment struts 49,50 and attached to the distal attachment struts 51,52 to serve a similar orientation and stabilization function. An integral barb 25 is located about the commissural bends 27,28 that interconnect the longitudinal attachment struts 49,50. The parallel longitudinal attachment struts 49,50 are also interconnected about their distal ends by a short interconnecting strut 81 such that an elongate closed cell 92 is formed. The width of cell 92 is not critical, although it may be made sufficiently narrow such that it serves to further pin or anchor the leaflets 60,61 to the struts 49,50, which could be especially advantageous in fixation if the leaflet material retracts during the remodeling process. A preferred width between the two struts 49,50 would be between 0-5 mm, with 0-3 mm being more preferred and 0-1 mm being most preferred. If the spacing is too wide, gaps may be created between the opposing leaflets which could allow for an unacceptable amount of reflux through the valve.

Figure 17:
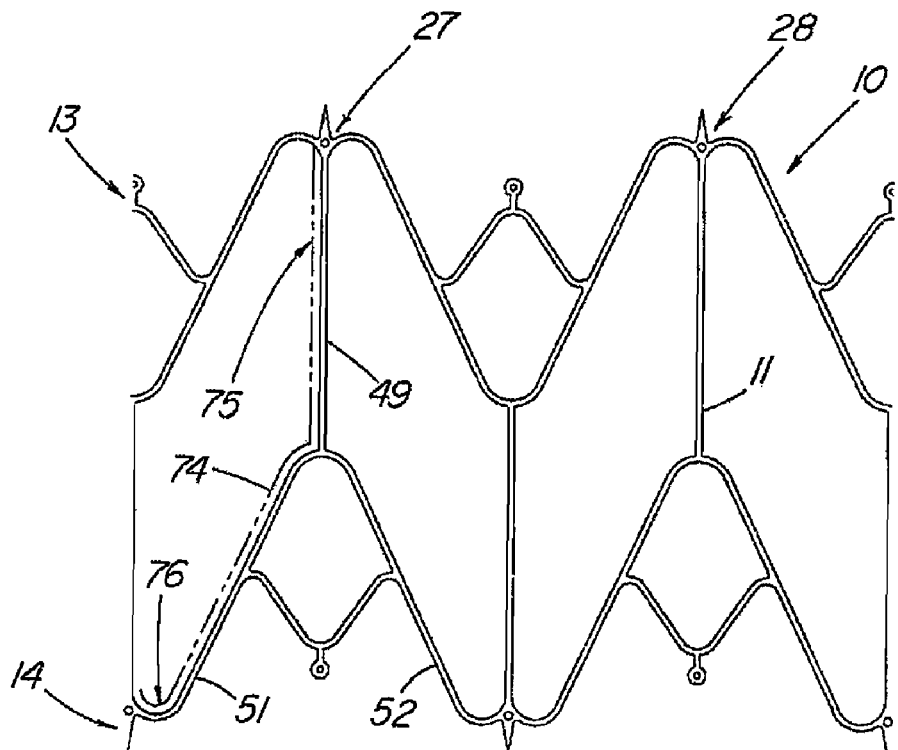
FIGS. 17-18 depict unrolled views of additional embodiments of the present invention for increasing the area of leaflet coaptation.

A similar frame design is shown in FIG. 17 which includes a single longitudinal attachment strut 49 to which both leaflets 60,61 are sewn or otherwise attached allowing for similar extended coaptation between leaflets. The leaflets 60,61 can be attached such that each abuts the strut 49 (and sewn or attached without being wrapped over the strut) or the first lateral leaflet edge (not shown) is wrapped around the strut 49 while the second leaflet lateral edge of the opposite leaflet is sewn over the first lateral leaflet edge and strut 49. The single attachment strut can be of a width that is generally uniform with respect to the other support structure or it may be made substantially thicker, such as shown in FIG. 19. Furthermore, a thicker strut 49 could include apertures 93 or slots of any shape or length distributed therealong for receiving sutures or other attachment elements 30, such as clips, rings, etc., for affixing or anchoring the leaf outer edges thereto. FIG. 20 depicts an embodiment having a pair of longitudinal attachment struts 49,50 with anchoring structure 95, such as the illustrative scalloped edge that is strategically configured therealong to help prevent or limit the attachment element 97 and the valve structure itself, from sliding down the longitudinal attachment struts 49,50, especially during any retraction that may occur with a bioremodelable material. The anchoring structure can comprise any projections or other structure that provides a shoulder or irregularities along the edges of the struts that helps limit sliding of the leaflets along the longitudinal attachment struts 49,50. Further examples of adaptations for limiting movement or migration of attachment elements (e.g., sutures) and covering material are disclosed in an application to Case et al. (U.S. Ser. No. 10/820,918), entitled 'Intraluminal Support Device with Graft' and filed Apr. 8, 2004, which is expressly incorporated by reference herein.

Figure 18:
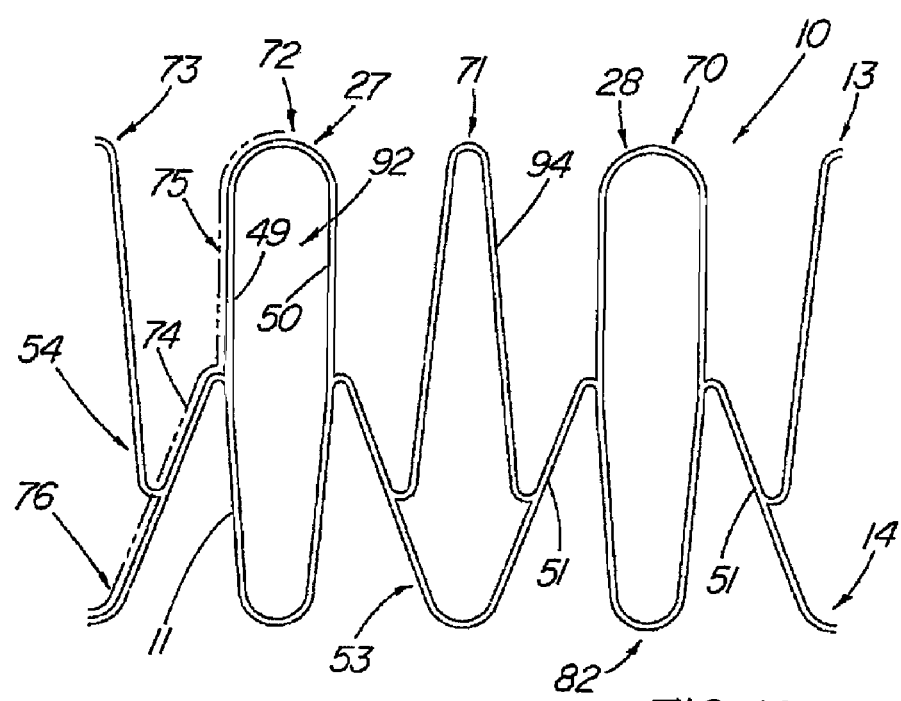

FIG. 18 depicts an embodiment having generally, but not absolutely parallel longitudinal attachment struts 49,50 which slightly converge toward the distal end 14 of the prosthesis 10 (and are spaced more distant from each other than the embodiment of FIGS. 13-14. The commissural bends 27,28 and distal bends 82 interconnect the longitudinal attachment struts and form a closed cell 92 as in the embodiment of FIGS. 13-16. The distal attachment struts 51,52 provide the interconnection between the opposite closed cells 92 as well as the distal portion 76 of the attachment pathway 74. They also carry a lateral arm 93 and together comprise the lateral support structure 83,84 that provide longitudinal support/stabilization and leaflet protection. The embodiment of FIG. 18 lacks proximal support arms 77,78 of the embodiment of FIGS. 13-16.

The illustrative support structure 11 in FIGS. 9, 11, 13-18 is not critical to achieve the optimal leaflet angles in the valve structure 12 for creating larger pockets, as depicted. For example, the attachment pathway 74 of the valve structure 12 can comprise an attachment to an outside support frame to form the illustrative configuration with the frame 32 that is not necessarily extending along the outer edges 39 of the leaflets 60,61, but rather attached to selected strut that cross the attachment pathway 74, especially along the distal portion 76 of the pathway. Furthermore, at least a portion of the outer edges 39 can be directly affixed to the vessel wall (such as being sutured, heat welded, or anchored with barbs, adhesives, etc.) with the frame 11 being absent or reinforcing or shaping only a limited portion of the leaflet outer edges 39, thus allowing for the vein to naturally collapse (at least partially) when not filled with blood. In the example depicted in FIG. 21, the frame 11 comprises a partial support 98 of a hair-pin configuration that includes a proximal bend about each commissure 27,28 with free-ended longitudinal attachment struts 49,50 extending therefrom which help form the leaflet angle 47, while the distal portion 76 of the attachment pathway 74 comprises an alternative attachment that does not result in the leaflet material being urged thereagainst by a radially expandable frame. Methods include surgical attachment, tissue welding, adhesives, barbs and other well-known methods, teachings of which is included in a co-pending U.S. patent application entitled, 'Percutaneously Deployed Vascular Valves with Wall-Adherent Adaptations (Case et al.) filed Apr. 1, 2004 (Ser. No. to be added by amendment), the disclosure of which is expressly incorporated by reference herein. The angle of the leaflets 60,61 relative to the longitudinal axis 64 of the prosthesis and vessel (half of the first angle 47 or α/2) is preferably −5-15° with a more preferred angle of 0-10° and a most preferred angle of 0-5°. The relatively small or shallow angles of the longitudinal attachment struts 49,50 about the commissures 27,28 allows for a larger space adjacent the leaflets 60,61 and broader pockets 35 at the base of the leaflets. The longitudinal attachment struts 49,50 of the support structure can be formed generally parallel to one another along the proximal portions of the longitudinal attachment struts 49,50 to create the maximum pocket size and greater coaptation of the leaflets. For example, the pocket 35 areas would be maximized in an attachment pathway 74 where angle 47 is zero (or a negative angle) and angle 48 is at least 90°, such that the attachment pathway along each leaflet lateral outer edge 87,88 is generally L-shaped such that the distal portion 76 of the attachment pathway angles abruptly from the proximal portion rather than assuming a dog-leg configuration as shown in the illustrative embodiments.

The amount of contactable or coaptable area 57 can be expressed in different ways. In the present invention, the length of the leaflet contact area 57 (or proximal portion 75 of the attachment pathway) in a typical venous valve prosthesis is preferably at least 2 mm and as much as 50 mm (depending on the configuration of the valve prosthesis), with a more preferred length of 5-30 mm and a most preferred range of 5-15 mm. In an average sized venous valve having a length of 25 mm, the preferred range of the leaflet contact area 57 or proximal attachment pathway 75 would be 10-80% of the prosthesis length (2.5-20 mm), assuming the valve structure 12 is generally as long as the support frame 11. A more preferred leaflet contact area 57 would comprise 30-60% with 35-55% being most preferred in a prosthesis of the same general type as depicted. The relationship between leaf contact area and the diameter of the vessel may be a factor in optimizing the functionality of the valve prosthesis 10. Preferably, the length of the longitudinal attachment struts 49,50 and/or leaflet contact area 57 is 25 to 250% of the nominal vessel diameter with a more preferred range of 25-150%.

The amount of slack in the leaflet material also helps determine how well the leaflets coapt during retrograde flow and how large of an opening they permit during antegrade flow. Preferably, but not essentially, the prosthesis is configured such that the distance formed between the leaflets in their fully open position and the vessel diameter remains preferably between 0-100% of the vessel diameter, with a more preferred range of 20-80% of the vessel diameter and a most preferred range of 50-70%. By substantially orienting the longitudinal attachment struts 49,50 with the longitudinal axis 64 of the prosthesis, less slack is necessary for optimal or extended coaptation. Not having the leaflets regularly contact the outer walls of the vessel can be especially important when using a bioremodelable material, such as an ECM, which can partially or completely adhere to the wall over time as tissue grows into the leaflets, thus compromising the functionality of the valve.

FIG. 12 depicts an embodiment having different structural configuration to alter retrograde fluid flow patterns within the pocket to prevent pooling of blood or bodily fluid. The support structure 11 includes proximal and distal sections 15,17 which are sized and configured to expand and engage the walls 38 when the valve prosthesis 10 is deployed within the bodily passage 20. The intermediate section 16, which includes the valve structure 12, is narrower than each of the adjoining proximal and distal sections 15,17. A covering of biologically-derived or synthetic biocompatible or bioremodelable material 44, such as a collagenous extracellular matrix (ECM) (e.g., SIS), pericardial tissue, or fabric, such as DACRON, ePTFE, etc., is attached over or inside the support structure to enclose passageway 62 and to help seal the prosthesis with the vessel. The proximal and distal sections 15,17 are generally frustoconical or bowl-shaped with the interface 46 with the proximal or distal end of the intermediate section 16 being smaller in diameter than the proximal or distal ends 13,14 of the prosthesis. By narrowing the passageway 62 of the prosthesis 10 at the point where it transitions between the proximal section 15 and the intermediate section 17, a Venturi effect is created in which the retrograde flow is accelerate, which advantageously produces enhanced flushing action (e.g., stronger vortices) within the pockets 35 surrounding the leaflets 60,61. The ability of the valve prosthesis 10 to prevent pooling of blood or fluid around the pockets 35 is further enhanced in the illustrative embodiment by configuring the leaflets 61,62 as in the example shown in FIG. 11. It is not necessary to the invention that the proximal and distal sections share the same configuration. The respective sections 15,16,17 may be separate, attached units, as shown, or represent subsections of a single anchoring portion 24, similar to the embodiment of FIG. 4.

It should be noted that the support structure and valve structure shown in each of the figures in the application are merely exemplary of the numerous well-known possibilities, many others of which are disclosed in U.S. patent application Ser. No. 10/642,372 entitled, 'Implantable Vascular Device,' filed Aug. 15, 2003 and whose disclosure is expressly incorporated by reference herein. For example, the valve structure may comprise more than the illustrative two leaflets or comprise leaflets of other shapes and configuration. The valve structure may also comprise a non-leaflet valve such as one or more tubular sleeves or other configurations adapted to restrict fluid flow. With regard to the support structure, it may be formed from wire, cut from a section of cannula, molded or fabricated from a polymer, biomaterial, or composite material, or a combination thereof. The pattern (i.e., configuration of struts and cells) of the anchoring portion(s) that is selected to provide radial expandability to the prosthesis is also not critical for an understanding of the invention. Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition.

The invention claimed is:

1. A valve prosthesis for deployment in a bodily passage, said valve prosthesis having a longitudinal axis, a prosthesis length, and comprising:
    a support structure having at least one longitudinal attachment strut generally aligned with said longitudinal axis and at least one distal attachment strut extending at an angle to said longitudinal axis; and
    a valve structure comprising a first leaflet having first proximal and first distal portions, first and second outer lateral edges, a first free inner edge, and a first inner surface extending from the first outer lateral edge to the second outer lateral edge and including the first free inner edge, and a second leaflet having second proximal and second distal portions, third and fourth outer lateral edges, a second free inner edge, and a second inner surface extending from the third outer lateral edge to the fourth outer lateral edge and including the second free inner edge, the first and second proximal portions attached to the at least one longitudinal attachment strut and cooperatively defining a leaflet contact area comprising a longitudinal portion along the valve structure having a length that is greater than or equal to 10% of said prosthesis length and in which the first and second inner surfaces coapt from the first and third outer lateral edges to the second and fourth outer lateral edges while the valve structure is in a resting state, the first and second distal portions attached to the at least one distal attachment strut.

2. A valve prosthesis according to claim 1, wherein the leaflet contact area has a length that is between 10 and 80% of said prosthesis length.

3. A valve prosthesis according to claim 1, wherein the leaflet contact area has a length that is between 30 and 60% of said prosthesis length.

4. A valve prosthesis according to claim 1, wherein the leaflet contact area has a length that is between 35 and 55% of said prosthesis length.

5. A valve prosthesis according to claim 1, wherein the leaflet contact area has a length that is greater than 50% of said prosthesis length.

6. A valve prosthesis according to claim 1, wherein the at least one longitudinal attachment strut comprises first and second longitudinal attachment struts disposed on opposite sides of the support structure.

7. A valve prosthesis according to claim 1, wherein the at least one longitudinal attachment strut comprises first and second pairs of longitudinal attachment struts disposed on opposite sides of the support structure.

8. A valve prosthesis according to claim 7, wherein the first pair of longitudinal attachment struts comprises first and second members and the second pair of longitudinal attachment struts comprises third and fourth members; and wherein the first proximal portion is attached to the first and third members and the second proximal portion is attached to the second and fourth members.

9. A valve prosthesis according to claim 7, wherein at least one of the first and second pairs of longitudinal attachment struts defines an elongate closed cell in the support structure.

10. A valve prosthesis according to claim 9, wherein a portion of at least one of the first and second proximal portions is disposed in the elongate closed cell.

11. A valve prosthesis according to claim 9, wherein a portion of the first proximal portion and a portion of the second proximal portion are disposed in the elongate closed cell.

12. A valve prosthesis according to claim 1, wherein the at least one distal attachment strut comprises an extension of the at least one longitudinal attachment strut.

13. A valve prosthesis according to claim 1, wherein the at least one distal attachment strut extends laterally outward from the at least one longitudinal attachment strut.

14. A valve prosthesis according to claim 1, wherein the at least one longitudinal attachment strut and the at least one distal attachment strut define a leaflet attachment pathway that includes an obtuse angle.

15. A valve prosthesis for deployment in a bodily passage, said valve prosthesis having a longitudinal axis, a prosthesis length, and comprising:
    a support structure having first and second longitudinal attachment struts and first and second distal attachment struts, the longitudinal attachment struts being generally aligned with said longitudinal axis and disposed on opposite sides of the support structure and each of the first and second distal attachment struts extending at an angle to said longitudinal axis; and
    a valve structure comprising a first leaflet having first proximal and first distal portions, first and second outer lateral edges, a first free inner edge, and a first inner surface extending from the first outer lateral edge to the second outer lateral edge and including the first free inner edge, and a second leaflet having second proximal and second distal portions, third and fourth outer lateral edges, a second free inner edge, and a second inner surface extending from the third outer lateral edge to the fourth outer lateral edge and including the second free inner edge, the first and second proximal portions attached to the first and second longitudinal attachment struts and cooperatively defining a leaflet contact area comprising a longitudinal portion along the valve structure having a length that is greater than or equal to 10% of said prosthesis length and in which the first and second inner surfaces coapt from the first and third outer lateral edges to the second and fourth outer lateral edges while the valve structure is in a resting state, each of the first and second distal portions attached to one of the first and second distal attachment struts.

16. A valve prosthesis according to claim 15, wherein the leaflet contact area has a length that is between 10 and 80% of said prosthesis length.

17. A valve prosthesis according to claim 15, wherein the leaflet contact area has a length that is between 30 and 60% of said prosthesis length.

18. A valve prosthesis according to claim 15, wherein the leaflet contact area has a length that is between 35 and 55% of said prosthesis length.

19. A valve prosthesis according to claim 15, wherein the leaflet contact area has a length that is greater than 50% of said prosthesis length.

* * * * *